US009220825B2

(12) United States Patent
Buckberry

(10) Patent No.: US 9,220,825 B2
(45) Date of Patent: Dec. 29, 2015

(54) BLOOD PUMP

(75) Inventor: Clive Buckberry, Warwick (GB)

(73) Assignee: Quanta Fluid Solutions Ltd., Warwickshire (GB)

(*) Notice: Subject to any disclaimer, the term of this patent is extended or adjusted under 35 U.S.C. 154(b) by 0 days.

(21) Appl. No.: 14/378,837

(22) PCT Filed: Feb. 16, 2012

(86) PCT No.: PCT/GB2012/050355
§ 371 (c)(1),
(2), (4) Date: Nov. 3, 2014

(87) PCT Pub. No.: WO2013/121163
PCT Pub. Date: Aug. 22, 2013

(65) Prior Publication Data
US 2015/0112119 A1    Apr. 23, 2015

(51) Int. Cl.
*A61M 1/10*    (2006.01)
(52) U.S. Cl.
CPC ............. *A61M 1/1087* (2014.02); *A61M 1/106* (2013.01); *A61M 1/1046* (2013.01)
(58) Field of Classification Search
CPC ... A61M 1/10; A61M 1/1037; A61M 1/1046; A61M 1/1087; A61M 1/106–1/1065
See application file for complete search history.

(56) References Cited

U.S. PATENT DOCUMENTS 5,458,468 A    10/1995    Ye et al.
2009/0137940 A1    5/2009    Orr

FOREIGN PATENT DOCUMENTS

JP    2009-533154 (A)    9/2009
WO    WO 2011/027118 A1    3/2011

OTHER PUBLICATIONS

Oct. 16, 2012 International Search Report for PCT/GB2012/050355.
Aug. 28, 2014 Transmittal of Int'l. Preliminary Report on Patentability of PCT/GB2012/050355.
Oct. 13, 2015 Japanese Office Communication in connection with JP 2014-557116.

*Primary Examiner* — Scott Getzow
(74) *Attorney, Agent, or Firm* — Hahn Loeser & Parks, LLP

(57) ABSTRACT

A blood pump 2 comprising: a cartridge 4 having a concave recess 8 therein having a surface, and a flexible membrane 0 covering said recess, the concave recess and flexible membrane forming a pump chamber 12 having an inlet 14 and an outlet 16 wherein: said flexible membrane is movable between a first position, separated from said surface wherein in such position the pump chamber has a maximum volume, and a second position, substantially adjacent said surface such that in said second position the pump chamber has a minimum volume, a pump driver mechanism 18 arranged to interface with the cartridge, said driver operable to move the flexible membrane in a first direction into the recess to, in use, pump blood from the chamber and operable to move the flexible membrane in a second direction away from the recess to, in use, draw blood into said chamber; and wherein the pump driver controls the movement of the flexible membrane in the first direction such that the speed at which it is moving reduces as it approaches the surface of the concave recess.

14 Claims, 2 Drawing Sheets

BLOOD PUMP

The present application is a §371 submission of international application No. PCT/ GB2012/050355, which was filed on 16 Feb. 2012 and entitled Blood Pump, and which was published in the English language on 22 Aug. 2013 with publication no. WO 2013/121163 A1.

The present invention relates to extracorporeal blood pumps, in particular to low hemolysis extracorporeal blood pumps.

Blood pumps for the extracorporeal circulation of blood are used in a number of medical applications, for example in hemodialysis. Commonly, blood is pumped in such circuits using peristaltic type pumps and, while these pumps are reliable and accepted within the medical industry, they do cause some hemolysis, resulting in a lowered hematocrit level. When returned to the patient after processing in the external circuit, the reduced hematocrit level reduces the patient's ability to effectively transport oxygen to the body. As a result of this many patients who have extracorporeal blood treatment, are treated with erythropoietin (EPO) to stimulate regeneration of new red blood cells to replace those damaged. In some conditions, such as dialysis wherein the patient needs to be treated with EPO to balance the hormonal requirement of the body, damage to blood cells results in an increase in the amount of EPO needed to be administered. Furthermore, when a patient has a naturally low hematocrit level due to a medical condition, for example end stage renal failure, damage to the red blood cells caused by treatment of the condition is particularly undesirable. In other extracorporeal blood processes such as aphaeresis, it is also important for the various blood cells to remain intact such that they can be effectively separated.

It is the purpose of the present invention to mitigate at least some of the above problems and to produce a means of blood pumping that minimises damage to blood cells.

According to the invention there is provided a blood pump comprising:
 a cartridge having a concave recess therein having a surface, and a flexible membrane covering said recess, the concave recess and flexible membrane forming a pump chamber, said pump chamber having an inlet and an outlet wherein: said flexible membrane is movable between a first position, separated from said surface wherein in such position the pump chamber has a maximum volume, and a second position, substantially adjacent said surface such that in said second position the pump chamber has a minimum volume,
 a pump driver mechanism arranged to interface with the cartridge, said driver operable to move the flexible membrane in a first direction into the recess to, in use, pump blood from the chamber and operable to move the flexible membrane in a second direction away from the recess to, in use, draw blood into said chamber; and
 wherein the pump driver controls the movement of the flexible membrane in the first direction such that the speed at which it is moving reduces as it approaches the surface of the concave recess.

By reducing the speed of the membrane as it approaches the surface of the concave recess shear forces acting on the blood cells as they accelerate through the reducing gap between the membrane and the surface of the concave recess are reduced therefore reducing damage to the blood cells.

In one preferred arrangement the inlet and the outlet form one common port in the concave surface.

Preferably the pump driver controls the movement of the membrane in the second direction such that the speed of the membrane is reduced as it approaches the first position.

By reducing the speed of the membrane as it approaches its first position fluid pressure spikes within the blood as the membrane reaches its first position and fluid flow into the pump stops is reduced, i.e. fluid hammer as the membrane stops is reduced.

Preferably the pump driver controls the movement of the membrane in the first direction such that the speed of the membrane is gradually increased from static in the first position. Alternatively, or in addition, the pump driver controls the movement of the membrane in the second direction such that the speed of the membrane is gradually increased from static in the second position.

By gradually increasing the speed of the membrane from its stopped position fluid pressure spikes within the blood are minimised as movement of the membrane in the first and/or second direction is initiated i.e. fluid hammer as the membrane starts to move is reduced.

Preferably the blood pump further comprises a controller, configured to control the pump driver to control the movement of the membrane.

Preferably the pump driver mechanism comprises drive fluid for applying fluid pressure to the membrane to move it between the first and second positions. More preferably the driver mechanism is arranged to apply a first pressure to move the membrane in the first direction and a second, lower, pressure to move the membrane in the second direction. Preferably the blood pump further comprises valve means controlled by the controller to vary the flow of the drive fluid to the membrane.

In a preferred arrangement the blood pump further comprises a blood inlet valve within the inlet and a blood outlet valve within the outlet, said blood inlet and outlet valves controlled by a controller, said controller configured to open and close the blood inlet and outlet valves such that when the membrane is moved in the first direction, the blood inlet valve is closed and the blood outlet valve is open, and to when the membrane is moved in the second direction, the blood inlet valve is open and the blood outlet valve is closed.

Preferably the membrane completes its movement in the first direction, and prior to commencing its movement in the second direction, the blood inlet valve is opened before the blood outlet valve is closed.

Preferably the membrane completes its movement in the second direction, and prior to commencing its movement in the first direction, the blood outlet valve is opened before the blood inlet valve is closed.

Preferably the blood outlet valve is opened prior to the membrane commencing movement in the first direction. Preferably the blood inlet valve is opened prior to the membrane commencing movement in the first direction.

The blood pump may be disposable.

Embodiments of the invention will now be described, by way of example only, with reference to the following drawings in which.

Figure 1:
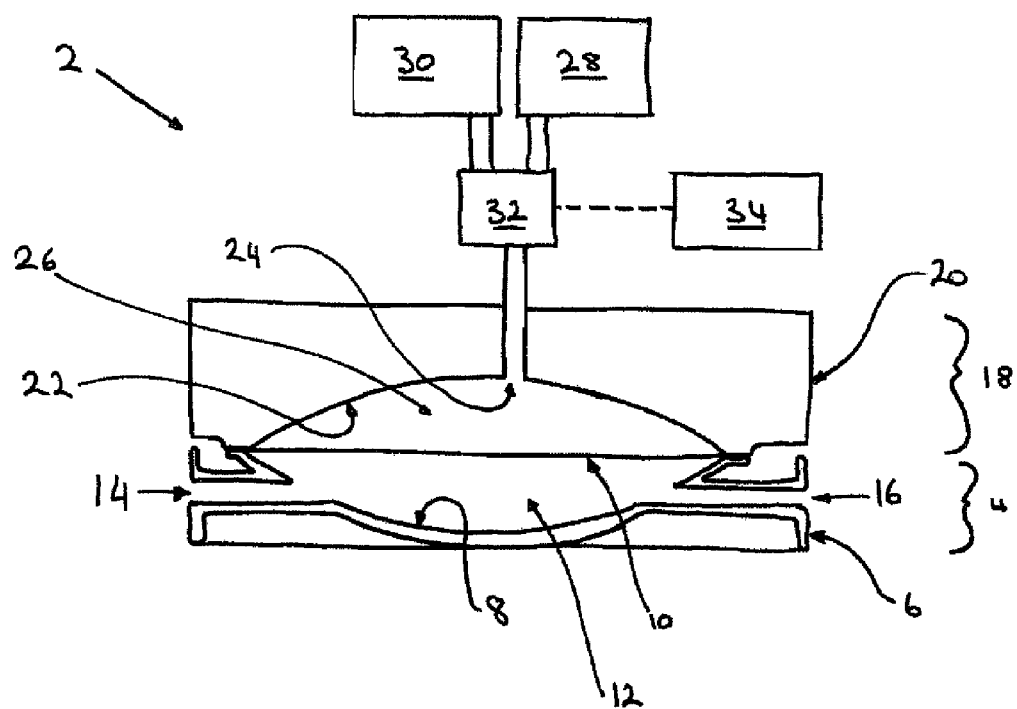
FIG. 1 is a diagram of a blood pump according to the present invention.

Referring to FIG. 1, a first embodiment of the invention provides a blood pump 2 comprising a pump cartridge 4 comprising a plastic shell 6 having concave recess 8 covered by a flexible membrane 10. The recess 8 and the flexible membrane 10 form a pump cavity 12 having an inlet 14 and an outlet 16 leading into and out of the cavity respectively. The cartridge 4 abuts a pump driver 18 comprising a platen 20 having a recessed surface 22 therein and a fluid port 24. In use the platen 20 sealingly engages with the cartridge 4 such that the recessed surface 22 and the flexible membrane 10 form a drive chamber 26. The fluid port 24 is connectable with a source of positive fluid pressure 28 and a source of negative fluid pressure 30 via a valve 32, controlled by a controller 34 to allow fluid to flow into or out of the drive cavity 26. The valve 32 is a proportional valve having a variable sized orifice therein, the valve controllable to change the size of the orifice, thereby controlling the flow therethrough. The positive 28 and negative 30 fluid sources are a pressure pump and a vacuum pump respectively. When the valve 32 is operated to allow fluid to flow into the drive chamber 26 from the source of positive fluid pressure 28, the membrane 10 is moved towards the recessed surface 8 and any blood that is in the pump cavity 12 is expelled via the outlet 16. When the valve 32 is operated to allow fluid to flow out of the drive chamber 26 to the source of negative fluid pressure 30, the membrane 10 is moved away from the recessed surface 8 and towards surface 22 and blood is drawn into the pump cavity 12 from the inlet 14.

In order to pump blood through the pump 2 the inlet 14 has an inlet valve (not shown) and the outlet 16 has an outlet valve (not shown) associated therewith. In operation, when the valve 32 is operated to allow fluid to flow into the drive chamber 26 from the source of positive fluid pressure 28 the inlet valve is closed and the outlet valve is open so the blood within the pump cavity 12 exits the outlet 16 via the outlet valve, and when the valve 32 is operated to allow blood to flow out of the drive chamber 26 to the source of negative fluid pressure 30, the inlet valve is open and the outlet valve is closed such that blood is drawn into the pump cavity 12 through the inlet 14 via the open inlet valve.

The inlet and outlet valves are operated in a manner to minimise pressure spikes within the fluid. When changing from filling to emptying the pump cavity 12, the outlet valve is opened before valve 32 is operated to allow fluid to flow into the drive chamber 26. In this manner there is no resistance against flow out of the outlet 16 during the brief time it takes the outlet valve to open and which would otherwise create a positive pressure spike within the blood, as the outlet valve is open before flow commences.

When changing from emptying to filling the pump cavity 12, the inlet valve is opened before valve 32 is operated to allow fluid to flow out the drive chamber 26. In this manner there is no resistance against flow into the pump cavity 12 via the inlet 14 during the brief time it takes the inlet valve to open and which would otherwise create a negative pressure spike within the blood, as the membrane 10 starts to move away from the recessed surface 8.

The inlet and outlet valves may be operated such that when the membrane 10 is at one extremity of its travel, either adjacent the concave recess 8 or adjacent the recessed surface 22, the valve, that is opening opens before the valve that is closing closes, i.e. both valves are momentarily open. For example, when positive pressure is applied to the membrane 10 it travels in the direction towards the concave recess 8, displacing blood through the outlet 16 via open outlet valve. Once the membrane 10 has reached the concave recess 8 the inlet valve is first opened, the outlet valve in the outlet 16 is then closed and then the valve 32 is operated to allow fluid to flow out of the drive chamber 26 such that the membrane starts to move in the direction away from the concave recess 8 and towards the recessed surface 22. In a similar manner, when the membrane 10 reaches the extremity of its travel adjacent the recessed surface 22, the outlet valve in the outlet 16 is first opened, the inlet valve in the inlet 14 is then closed, and the valve 32 is then operated to allow fluid to flow into the drive chamber 26 such that the membrane starts to move in the direction away from the recess surface 22 and towards the concave recess 8.

The controller 34 is operable to variably open the valve 32 such that as fluids starts to flow into, or out of, the chamber 12 the flow is initially slow and then builds. The controller 34 is also operable to variably close the valve 32 such that as the membrane 10 reaches the end of its movement fluid flow is gradually reduced and does not stop abruptly. By this method of operation fluid hammer within the blood, which causes rupture of red blood cells is avoided. Furthermore, as the membrane approaches the recessed surface 8 the blood flows through an ever reducing gap and therefore, if the membrane were to be operated at a single speed, would accelerate therethrough increasing fluid shear on the cells. Reducing the speed of the membrane at the end of the stroke reduces the severity of any shear forces and therefore causes less blood damage.

Figure 2:
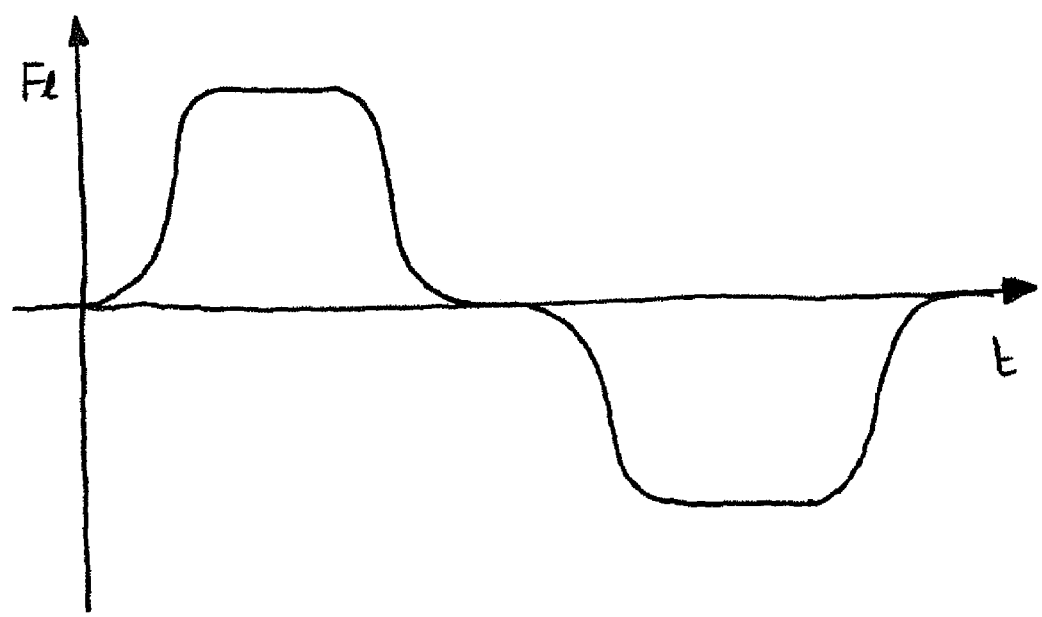
FIG. 2 is a graph showing flow against time of blood entering and exiting the pump chamber.

FIG. 2 shows a profile of the fluid flow into and out of the cavity where t=time and where Fl=flow.

In a second embodiment, the blood pump is a disposable blood pump comprising a disposable pump cartridge.

The description above is only one way of achieving the claimed invention and other methods will be obvious to the person skilled in the art, for example the proportional valve 32 could be replaced with a pulse width modulated valve without departure from the scope of the invention.

The invention claimed is:

1. A blood pump comprising:
a cartridge having a concave recess therein having a surface, and a flexible membrane covering said recess, the concave recess and flexible membrane forming a pump chamber, said pump chamber having an inlet and an outlet wherein: said flexible membrane is movable between a first position, separated from said surface wherein in such position the pump chamber has a maximum volume, and a second position, substantially adjacent said surface such that in said second position the pump chamber has a minimum volume,
a pump driver mechanism arranged to interface with the cartridge, said driver operable to move the flexible membrane in a first direction into the recess to, in use, pump blood from the chamber and operable to move the flexible membrane in a second direction away from the recess to, in use, draw blood into said chamber; and
wherein the pump driver controls the movement of the flexible membrane in the first direction such that the speed at which it is moving reduces as it approaches the surface of the concave recess.

2. The blood pump according to claim 1 wherein:
the pump driver controls the movement of the membrane in the second direction such that the speed of the membrane is reduced as it approaches the first position.

3. The blood pump according to claim 1 wherein:
the pump driver controls the movement of the membrane in the first direction such that the speed of the membrane is gradually increased from static in the first position.

4. The blood pump according to claim 1 wherein:
the pump driver controls the movement of the membrane in the second direction such that the speed of the membrane is gradually increased from static in the second position.

5. The blood pump according to claim 1 further comprising a controller, configured to control the pump driver to control the movement of the membrane.

6. The blood pump according to claim 1 wherein the pump driver mechanism comprises drive fluid for applying fluid pressure to the membrane to move it between the first and second positions.

7. The blood pump according to claim 6 wherein the pump driver mechanism is arranged to apply a first pressure to move the membrane in the first direction and a second, lower, pressure to move the membrane in the second direction.

8. The blood pump according to claim 7 further comprising valve means controlled by the controller to vary the flow of the drive fluid to the membrane.

9. The blood pump according to claim 1 further comprising a blood inlet valve within the inlet and a blood outlet valve within the outlet, said blood inlet and outlet valves controlled by a controller, said controller configured to open and close the blood inlet and outlet valves such that when the membrane is moved in the first direction, the blood inlet valve is closed and the blood outlet valve is open, and when the membrane is moved in the second direction, the blood inlet valve is open and the blood outlet valve is closed.

10. The blood pump according to claim 9 wherein when the membrane completes its movement in the first direction, and prior to commencing its movement in the second direction, the blood inlet valve is opened before the blood outlet valve is closed.

11. The blood pump according to claim 9 wherein when the membrane completes its movement in the second direction, and prior to commencing its movement in the first direction, the blood outlet valve is opened before the blood inlet valve is closed.

12. The blood pump according to claim 9 wherein the blood outlet valve is opened prior to the membrane commencing movement in the first direction.

13. The blood pump according to claim 9 wherein the blood inlet valve is opened prior to the membrane commencing movement in the first direction.

14. The blood pump according to claim 1 wherein the blood pump is disposable.

\* \* \* \* \*